US011369709B2

(12) United States Patent
Hsiao

(10) Patent No.: US 11,369,709 B2
(45) Date of Patent: Jun. 28, 2022

(54) ELECTRICAL WALL SOCKET MOUNTED AROMA DIFFUSER WITH A CARRIER LOADED AROMATIC BOTTLE

(71) Applicant: DONGGUAN YIH TEH ELECTRIC PRODUCTS CO., LTD., Dongguan (CN)

(72) Inventor: Ming Jen Hsiao, Miaoli County (TW)

(73) Assignee: DONGGUAN YIH TEH ELECTRIC PRODUCTS CO., LTD., Dongguan (CN)

( * ) Notice: Subject to any disclaimer, the term of this patent is extended or adjusted under 35 U.S.C. 154(b) by 468 days.

(21) Appl. No.: 16/506,473

(22) Filed: Jul. 9, 2019

(65) Prior Publication Data

US 2019/0328922 A1    Oct. 31, 2019

Related U.S. Application Data

(63) Continuation-in-part of application No. 15/866,181, filed on Jan. 9, 2018, now Pat. No. 10,842,901.

(51) Int. Cl.
*A61L 9/03* (2006.01)
*H01R 33/02* (2006.01)

(52) U.S. Cl.
CPC .............. *A61L 9/03* (2013.01); *H01R 33/02* (2013.01); *A61L 2209/133* (2013.01)

(58) Field of Classification Search
CPC .............. A61L 9/03-037; A61L 2209/133
USPC .................................................. D23/60-363
See application file for complete search history.

(56) References Cited

U.S. PATENT DOCUMENTS

| 4,734,560 | A | * | 3/1988 | Bowen | A01M 1/2077 |
| | | | | | 392/390 |
| 5,505,236 | A | * | 4/1996 | Grabenkort | A61M 16/183 |
| | | | | | 128/202.27 |
| 8,066,420 | B2 | | 11/2011 | Hsiao | |
| 8,133,059 | B1 | | 3/2012 | Hsiao | |
| 8,147,097 | B1 | | 4/2012 | Hsiao | |
| 8,192,041 | B2 | | 6/2012 | Hsiao | |
| 8,765,073 | B1 | | 7/2014 | Shbvi | |
| 8,787,739 | B2 | | 7/2014 | Shbvi | |
| 8,983,277 | B2 | | 3/2015 | Hsiao | |
| 9,031,392 | B2 | | 5/2015 | Shbvi | |
| 9,206,963 | B2 | | 12/2015 | Hsiao | |
| 9,410,695 | B2 | | 8/2016 | Hsiao | |
| 9,498,553 | B2 | | 11/2016 | Shbvi | |

(Continued)

*Primary Examiner* — Erin E McGrath
(74) *Attorney, Agent, or Firm* — Sinorica LLC

(57) ABSTRACT

An electrical wall socket mounted aroma diffuser with a carrier loaded aromatic bottle is disclosed. The carrier of the carrier loaded aromatic bottle uses capillary pores to absorb the aromatic fluid so that the aromatic fluid will not flow out of the aroma diffuser even if the aroma diffuser dumps. When the aromatic fluid is used up, a new aromatic fluid can be easily and quickly added to the carrier for application. Therefore, the electrical wall socket mounted aroma diffuser of the invention is safe to use. The carrier can be used repeatedly with a new supply of aromatic fluid. It does not need to clean the part of the aroma diffuser that accommodates the aromatic fluid. The user can detach the carrier loaded aromatic bottle from the bottle holder for the replacement of another carrier loaded aromatic bottle that is filled up with a different smell of aromatic fluid.

10 Claims, 6 Drawing Sheets

(56) References Cited

U.S. PATENT DOCUMENTS

| | | | |
|---|---|---|---|
| 2003/0138241 A1* | 7/2003 | Pedrotti | A01M 1/2077 |
| | | | 392/395 |
| 2005/0247802 A1* | 11/2005 | Varanasi | A61L 9/037 |
| | | | 239/44 |
| 2006/0219800 A1* | 10/2006 | Liu | A61L 9/037 |
| | | | 239/44 |
| 2011/0110824 A1 | 5/2011 | Hsiao | |
| 2014/0110389 A1 | 4/2014 | Shbvi | |
| 2014/0112649 A1* | 4/2014 | Irvin | A61L 9/03 |
| | | | 392/390 |
| 2015/0109823 A1 | 4/2015 | Hsiao | |
| 2015/0117056 A1 | 4/2015 | Hsiao | |
| 2016/0195257 A1 | 7/2016 | Hsiao | |

* cited by examiner

ELECTRICAL WALL SOCKET MOUNTED AROMA DIFFUSER WITH A CARRIER LOADED AROMATIC BOTTLE This application is a Continuation-in-Part of application Ser. No. 15/866,181, filed Jan. 9, 2018.

BACKGROUND OF THE INVENTION

1. Field of the Invention

The present invention relates to scent releasing devices and more specifically, to an electrical wall socket mounted aroma diffuser with a carrier loaded aromatic bottle.

2. Description of the Related Art

Aroma diffusers have some problems of heating the aromatic fluid, such as U.S. Pat. Nos. 8,066,420, and 8,147,166. These aroma diffusers include a power source, a heating source, and various essential liquid fragrances such as essential oils or waxes. If the aroma diffusers accidentally fall down, the heated essential oils or molten waves will flow out, causing an accident. Further, after the use, the user must manually remove the essential oil or fragrance residue from the container, and it takes time to clean the aroma diffuser. Further, the process of replacing the new essential oil or fragrance is slow and inconvenient. This is also a problem to be overcome. Further, in application, the high temperature of the heating source can be transferred to the control element, the electrical plug, or the other electrical or electronic components, causing damage or making the outside of the aroma diffuser hot.

SUMMARY OF THE INVENTION

The present invention has been accomplished under the circumstances in view. It is therefore an object of the present invention to provide an electrical wall socket mounted aroma diffuser with a carrier loaded aromatic bottle, which uses the capillary pores of the carrier of the carrier loaded aromatic bottle to absorb the aromatic fluid so that the aromatic fluid will not flow out of the aroma diffuser even if the aroma diffuser dumps. When the aromatic fluid is used up, a new aromatic fluid can be easily and quickly added to the carrier for application. Therefore, the electrical wall socket mounted aroma diffuser of the invention is safe to use.

It is another object of the present invention to provide an electrical wall socket mounted aroma diffuser with a carrier loaded aromatic bottle, which is designed with a thermal insulation structure to protect the aroma diffuser from heater temperature effects or damage.

To achieve these and other objects of the present invention, an electrical wall socket mounted aroma diffuser comprises a back cover, a thermal conduction unit, a heater, an electrical plug, a front cover and a bottle holder. The back cover is a hollow shell, comprising an opening defined in a front side thereof and a first hole located on an opposing back side thereof to face toward the opening. The front cover is fastened to the front cover to cover the opening. The front cover comprises a second hole. The bottle holder is fastened to an outer side of the front cover. The thermal conduction unit is mounted in the second hole of the front cover in flush with the front cover. The heater is mounted in the back cover and located at an inner side of the thermal conduction unit and kept in contact with the thermal conduction unit. The electrical plug is mounted in the first hole of the back cover and electrically connected with the heater. The electrical plug is to be connected to power supply. The heater is used to heat the thermal conduction unit. The heater is, for example, a resistor, a thermistor, a cement resistor or any of various heaters such as PTC.

The electrical wall socket mounted aroma diffuser further comprises a carrier loaded aromatic bottle. The carrier loaded aromatic bottle comprises a bottle body, a carrier, a bottle mouth and an aromatic fluid. The carrier is mounted inside the bottle body. The carrier comprises capillary pores for absorbing the aromatic fluid.

The carrier loaded aromatic bottle is detachably mounted in the bottle holder with one side thereof kept in contact with the outer side of the thermal conduction unit. The electrical plug is to be connected to a power source and is electrically connected to the heater. The power source is provided to the heater, causing the heater to generate heat that is transferred to the thermal conduction unit. The thermal conduction unit evenly distributes the heat energy and transfers the heat energy to the carrier loaded aromatic bottle to heat the carrier loaded aromatic bottle and the aromatic fluid in its carrier, causing the aromatic fluid to be vaporized into tiny aroma molecules that fly into the surrounding air. The thermal conduction unit of the electrical wall socket mounted aroma diffuser does not contact the front cover. It will not transfer heat source to the body of the electrical wall socket mounted aroma diffuser, providing a heat insulation effect and protecting the electrical wall socket mounted aroma diffuser against the thermal effect of the heater and avoiding damage.

Further, the carrier of the carrier loaded aromatic bottle of the electrical wall socket mounted aroma diffuser can be placed in the bottle body from the bottle mouth. Even if the electrical wall socket mounted aroma diffuser falls down during use or movement, the aromatic fluid in the carrier will not flow out of the carrier loaded aromatic bottle. When compared to conventional designs, the electrical wall socket mounted aroma diffuser is safer. Further, when the aromatic fluid is used up, the user can fill new aromatic fluid from the bottle mouth of the carrier loaded aromatic bottle into the carrier, enabling the capillary pores of the carrier to absorb the aromatic fluid for application. Thus, the user does not need to clean the aromatic fluid container of the electrical wall socket mounted aroma diffuser. It is easy and quick to add new aromatic fluid.

DETAILED DESCRIPTION OF THE PREFERRED EMBODIMENT

Figure 1:
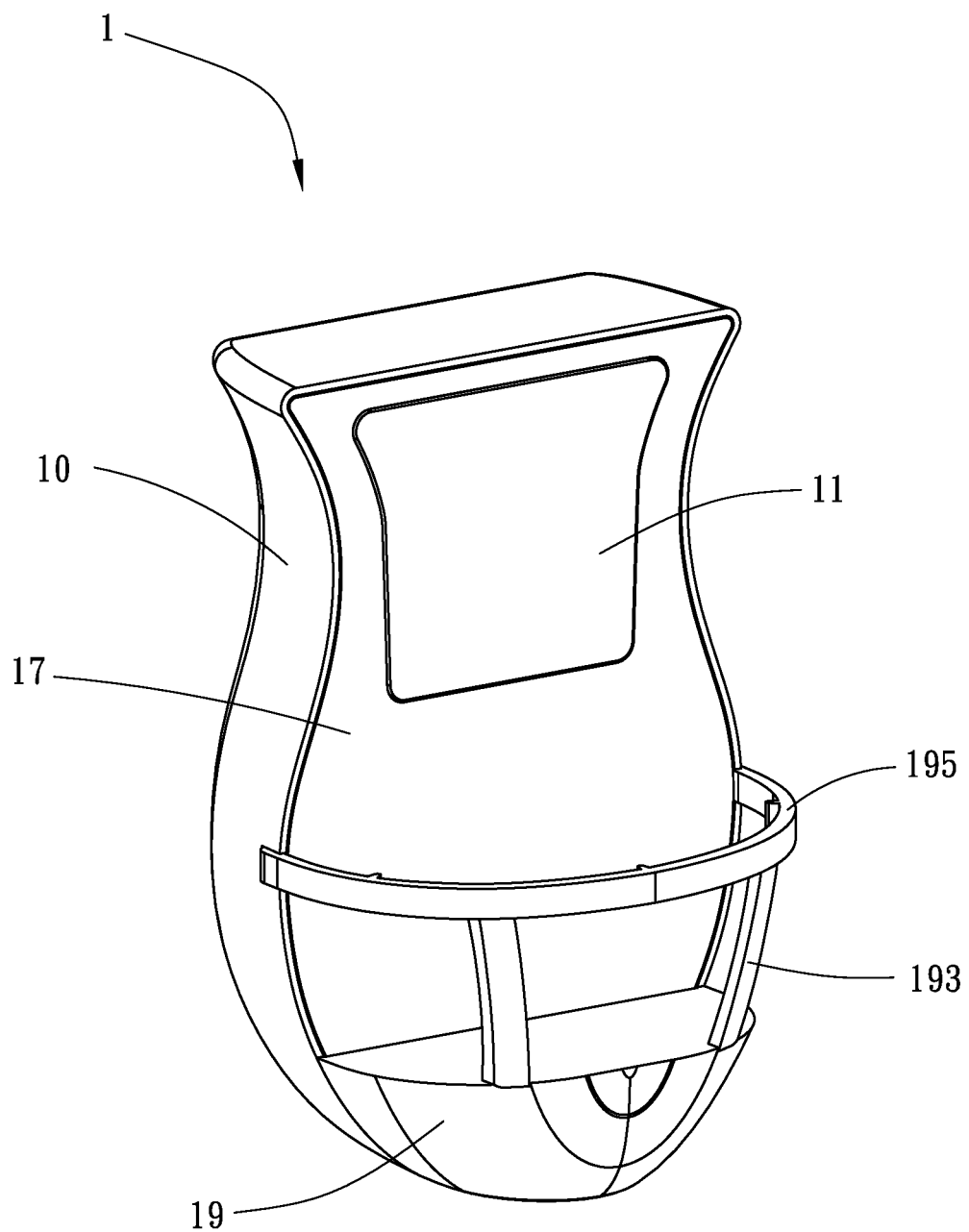
FIG. 1 is an oblique top elevation of an electrical wall socket mounted aroma diffuser in accordance with the present invention (the carrier loaded aromatic bottle excluded).
Figure 2:
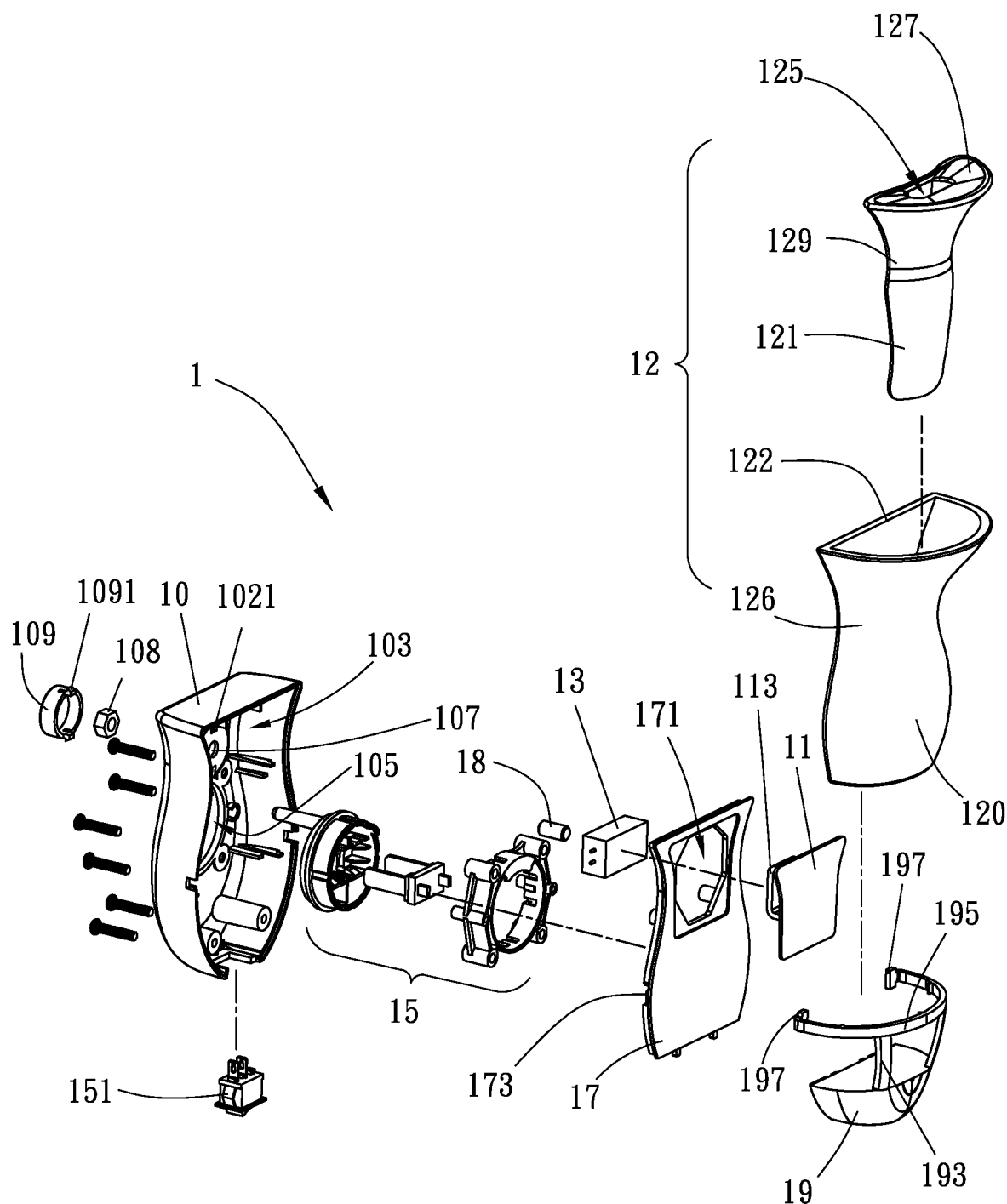
FIG. 2 is an exploded view of the electrical wall socket mounted aroma diffuser in accordance with the present invention.
Figure 3:
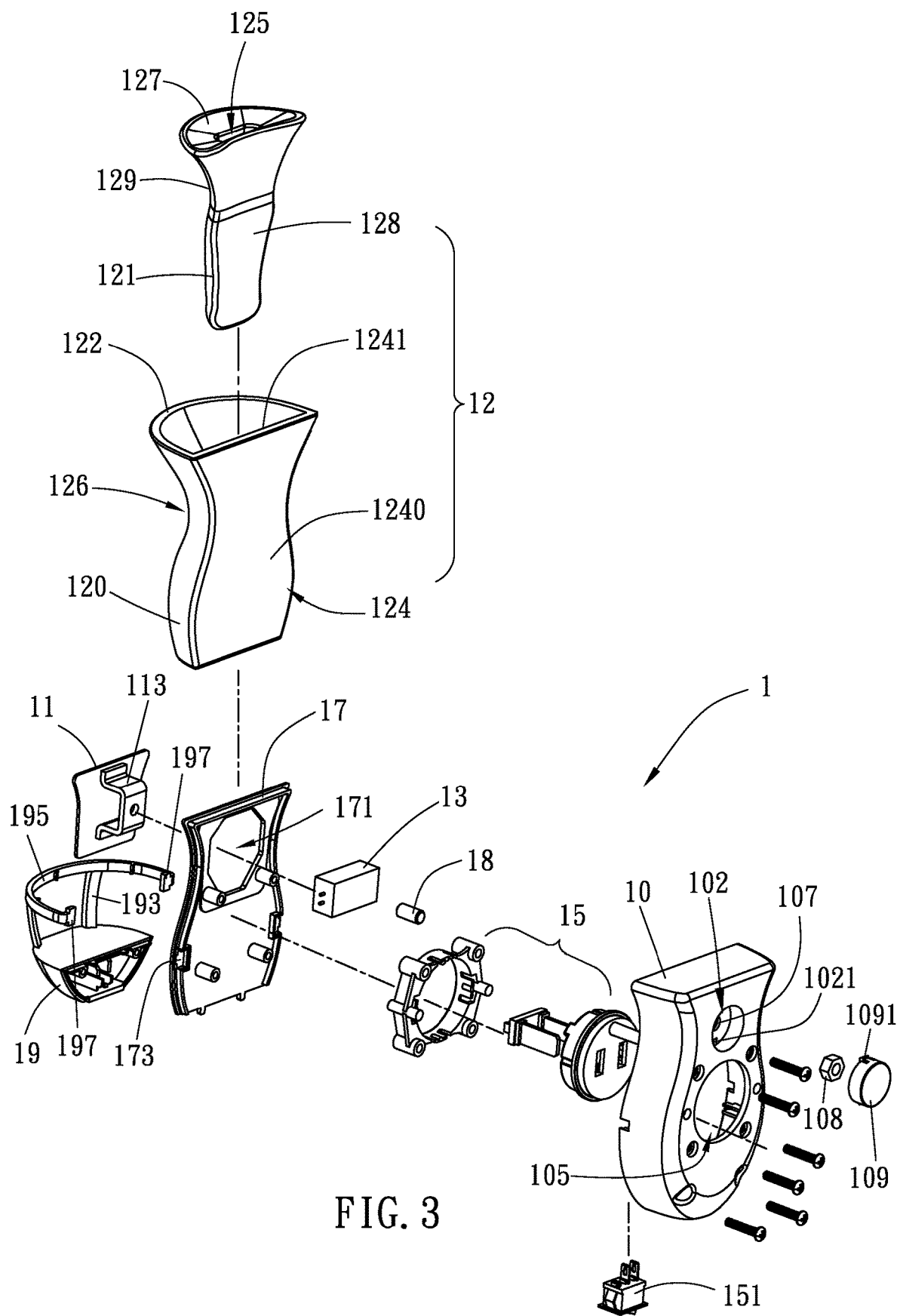
FIG. 3 corresponds to FIG. 2 when viewed from another angle.
Figure 4:
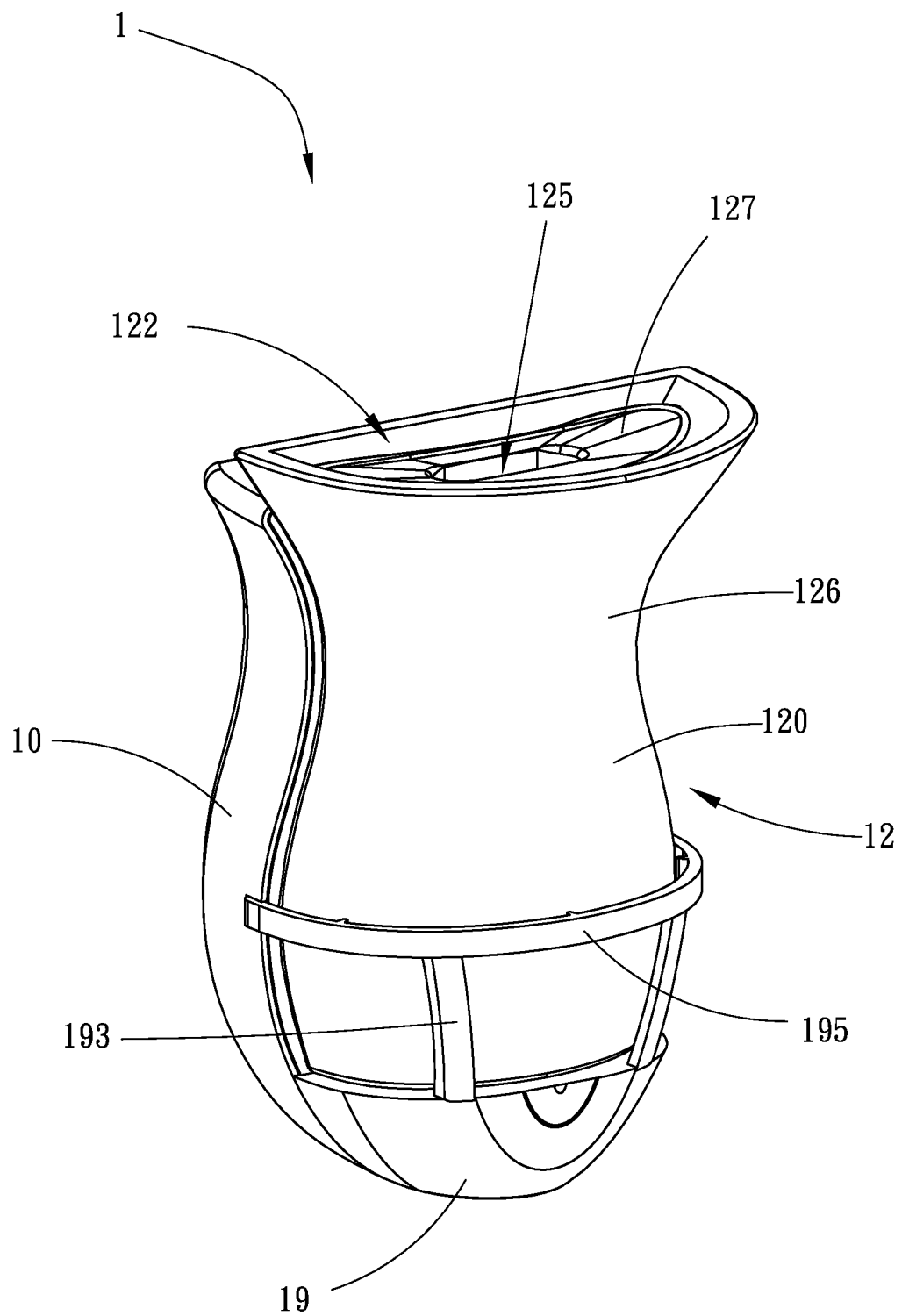
FIG. 4 is an oblique top elevation of the electrical wall socket mounted aroma diffuser of the present invention with the carrier loaded aromatic bottle installed.
Figure 5:
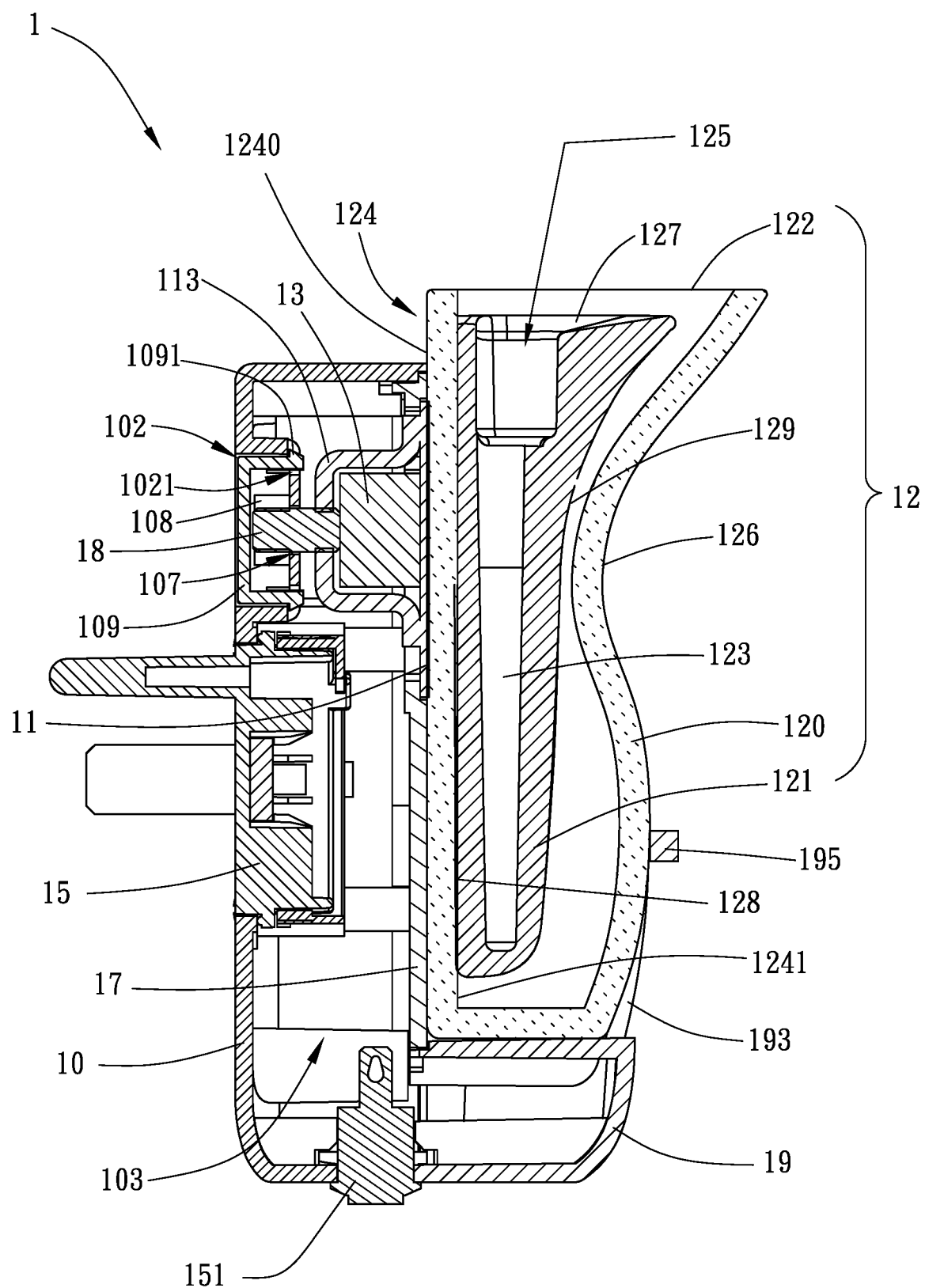
FIG. 5 is a sectional view of the electrical wall socket mounted aroma diffuser and the carrier loaded aromatic bottle in accordance with the present invention.

Referring to FIGS. 1-3, an electrical wall socket mounted aroma diffuser 1 in accordance with the present invention is shown. The electrical wall socket mounted aroma diffuser comprises a back cover 10, a thermal conduction unit 11, a heater 13, an electrical plug 15, a front cover 17, and a bottle holder 19.

The back cover 10 in this embodiment is a hollow shell, having an opening 103 and a first hole 105. The opening 103 is defined in a front side of the back cover 10. The first hole 105 is located on an opposing back side of the back cover 10 to face toward the opening 103. The front cover 17 has a second hole 171. The front cover 17 is fastened to the back cover 10 to cover the opening 103. The bottle holder 19 is fastened to the front cover 10 outside the back cover 10. The thermal conduction unit 11 is mounted in the second hole 171 of the front cover 17. The thermal conduction unit 11 does not touch the front cover 17. In this embodiment, the thermal conduction unit 11 is kept in flush with a front surface of the front cover 17. The heater 13 is mounted in the back cover 10 at an inner side relative to the thermal conduction unit 11. Further, the heater 13 is kept in contact with the thermal conduction unit 11. The electrical plug 15 is mounted in the first hole 105 of the back cover 10. The heater 13 is electrically connected to the electrical plug 15. In this embodiment, the electrical plug 15 is to be connected to power supply (electrical wall socket. The heater 13 is used to heat the thermal conduction unit 11. The heater 13 is, for example, a resistor, a thermistor, a cement resistor or any of various heaters such as PTC.

Referring to FIGS. 2-6, the electrical wall socket mounted aroma diffuser 1 further comprises a carrier loaded aromatic bottle 12. The carrier loaded aromatic bottle 12 comprises a bottle body 120 with a bottle mouth 122, a carrier 121, and an aromatic fluid (not shown). The carrier 121 is mounted in the bottle body 120. The carrier 121 has capillary pores to absorb the aromatic fluid. The aromatic fluid is siphoned by the capillary pores of the carrier 121 and does not flow out of the carrier 121. The carrier 121 loaded aromatic bottle 12 is detachably mounted in the bottle holder 19 and kept in contact with an outer surface of the thermal conduction unit 11. The electrical plug 15 is connected to power supply to provide electricity to the heater 13, causing the heater 13 to generate heat. Thus, heat generated by the heater 13 is evenly distributed in the thermal conduction unit 11 and transferred to the carrier 121 loaded aromatic bottle 12 to heat the bottle body 120 and the aromatic fluid in the carrier 121, causing the aromatic fluid to be volatilized into fine aromatic molecules that are dispersed out of the bottle mouth 122 of the bottle body 120 into the environment and mixed with air to produce aroma.

The carrier 121 of the carrier loaded aromatic bottle 12 can be placed from the bottle mouth 122 to the inside of the bottle body 120. Even if the carrier 121 loaded aromatic bottle 12 is tilted or dumped during use or movement, the aromatic fluid absorbed in the carrier 121 will not flow out of the carrier 121. With the use of the carrier 121 loaded aromatic bottle 12, the electrical wall socket mounted aroma diffuser is relatively safer in use when compared with prior art designs. Further, when the aromatic fluid of the electrical wall socket mounted aroma diffuser 1 is used up, the user only needs to inject a new aromatic fluid from the bottle mouth 122 into the bottle body 120 to contact the carrier 121, allowing the capillary pores of the carrier 121 to absorb the injected aromatic fluid. Thus, the user can use the electrical wall socket mounted aroma diffuser again without washing. Therefore, it is quick and easy to add new aromatic fluid.

In some embodiments of the present invention, the carrier 121 has capillary pores capable of capillary action of aromatic fluid, wherein the carrier 121 can be a variety of absorbers, the absorber can adsorb the aromatic fluid, store and prevent the aromatic fluid from flowing. The carrier 121 can be heated to transfer the temperature of the heat to the aromatic fluid in the capillary pores of the carrier 121, enabling the aromatic fluid to be volatilized into aroma molecules to escape and mix with the air. The carrier 121 can be, for example, a plastic having pores, such as PE plastic; or a porous ceramic, gypsum, suction core (cotton cloth, foam, cloth), fiber bundle, and the like.

The aforesaid thermal conduction unit 11 is a heat conductive material, and the thermal conduction unit 11 is selected from any one of, for example, metal or ceramic, glass, etc., whereby the heat source of the heater 13 is transmitted to the thermal conduction unit 11. In some embodiments of the present invention, the thermal conduction unit 11 is a metal piece, whereby the thermal conduction unit 11 uniformly and stably transfer heat source to the carrier 121 loaded aromatic bottle 12.

Referring to FIGS. 2, 3 and 5 again, in one embodiment of the present invention, the carrier 121 of the carrier loaded aromatic bottle 12 further comprises a fluid chamber 123 and a filling hole 125. The fluid chamber 123 is defined in the carrier 121. The filling hole 125 is on the upper side of the fluid chamber 123 in communication with the fluid chamber 123. With the filling hole 125, the user can inject the aromatic fluid into the interior of the fluid chamber 123. The capillary pores in the fluid chamber 123 of the carrier 121 absorb the aromatic fluid.

The fluid chamber of the carrier 121 of this embodiment is designed differently from the conventional absorbing carriers that absorb liquid from the outside direction, and the liquid will form a dirty state outside the general carriers, and at the same time, the amount of liquid that the user needs to pour into is harder to predict. The amount of the aromatic fluid that the carrier 121 can absorb can be estimated by making a test. Thereafter, the accommodation space of the fluid chamber 123 can be designed to fit the estimated amount of aromatic fluid. In this way, the user can inject an appropriate amount of the aromatic fluid into the fluid chamber 123 of the carrier 121.

In some embodiments of the present invention, the carrier 121 further comprises a funnel 127. The funnel 127 is formed on the upper edge of the carrier 121. The filling hole 125 is formed on the upper edge of the carrier 121 and is connected to the lower edge of the funnel 127. While the carrier 121 is disposed inside the bottle body 120, the funnel 127 is fitted inside the bottle mouth 122. When the user injects the aromatic fluid, the aromatic fluid flows smoothly through the funnel 127 into the filling hole 125 and the fluid chamber 123 and then absorbed by the capillary pores of the carrier 121.

Referring to FIGS. 2-6 again, in one embodiment of the present invention, the bottle body 120 comprises a planar wall 124 formed on one side thereof. The planar wall 124 defines an inner wall 1241 and an outer wall 1240. In this embodiment, the inner wall 1240 of the planar wall 124 is formed on the inner side of the bottle body 120, and the outer wall 1241 of the planar wall 124 is formed on the outer side of the bottle body 120. The inner wall 1241 and the outer wall 1240 are disposed corresponding to each other to form a planar wall structure. The carrier 121 further comprises a contact plane 128 formed on one side thereof. The contact plane 128 is used to planarly contact the inner wall 1241 of the planar wall 124 during heat conduction. The carrier loaded aromatic bottle 12 is detachably mounted in the bottle holder 19. In this embodiment, the thermal conduction unit 11 is selected from a metal piece. The outer wall 1240 of the planar wall 124 is used to planarly contact the outer surface of the metal piece of the thermal conduction unit 11. The carrier loaded aromatic bottle 12 can effectively receive the heat source of the heater 13 to the metal piece by the planar wall 124 for effective heat conduction to the contact plane 128 to heat the aromatic fluid in the pores of the carrier 121 to generate aroma molecules.

Referring to FIGS. 2-6, in one embodiment of the present invention, the bottle body 120 has a convergent portion 126 formed on a part thereof. The carrier 121 further comprises a neck 129 disposed at a bottom side of the funnel 127. Thereby, when the carrier 121 is placed inside the bottle body 120 from the bottle mouth 122, the neck 129 is just detachably fitted into the convergent portion 126 of the bottle body 120. Thus, the carrier 121 will not fall out of the bottle body 120 even if the carrier loaded aromatic bottle 12 is moved or dumped.

Referring to FIGS. 2, 3 and 5 again, the electrical wall socket mounted aroma diffuser further comprises connection means 18. The connection means 18 is any one of a screw, a fixing rod or a fixing frame, for example. The back cover 10 further comprises a screw hole 107 located on an opposing back side thereof adjacent to the first hole 105. The thermal conduction unit 11 comprises a screw holder 113 formed on an inner side thereof. The screw holder 113 has a hole for the passing of the connection means 18. The heater 13 is disposed between the screw holder 113 and the inner side of the thermal conduction unit 11. The connection means 18 has one end thereof fastened to the screw hole 107, and an opposite end thereof inserted through the screw holder 113 and stopped at the heater 13 against the thermal conduction unit 11. In this manner, the opposite end of the connection means 18 is inserted through the screw holder 113 to hold down the heater 13 and the thermal conduction unit 11, and the thermal conduction unit 11 is protruded forwardly slightly above the second hole 171 of the front cover 17 a tiny height. Thereby, thermal conduction unit 11 does not contact the front cover 17 to insulate the high temperature of the heater 13, avoiding the high temperature conduction of the heater 13 to the electrical wall socket mounted aroma diffuser 1 and its electrical or electronic components (not shown) or the electrical plug 15 to maintain good performance and to prevent damage.

The electrical wall socket mounted aroma diffuser 1 further comprises a nut 108 and a tamper buckle 109. The tamper buckle 109 comprises at least one movable fastening member 1091. The back cover 10 further comprises a locating hole 102. The locating hole forms therein a retaining groove 1021. The locating hole 102 is disposed in communication with the screw hole 107. The connection means 18 in this embodiment is a screw rod. The screw rod of the connection means 18 has one end thereof threaded into the screw hole 107 and the locating hole 102. The nut 108 is threaded on the screw rod of the connection means 18. The tamper buckle 109 is mounted in the locating hole 102 and fastened to the outer side of the nut 108 with the movable fastening member 1091 secured to the retaining groove 1021.

Therefore, the tamper buckle 109 cannot be disassembled by the general user or the child, and the electrical wall socket mounted aroma diffuser 1 is prevented from being separated by the tamper buckle 109, which is safer.

Referring to FIGS. 1-4 again, in one embodiment of the present invention, the bottle holder 19 comprises a base 191 and a fence 193. The fence 193 comprises an arched rail 195. The arched rail 195 has two opposite ends thereof respectively terminating in a hook 197. The front cover 17 has two hook grooves 173 respectively located on two opposite side edges thereof. The bottle holder 19 is fastened to the front cover 17 by hooking the hooks 197 in the respective hook grooves 173.

Figure 6:
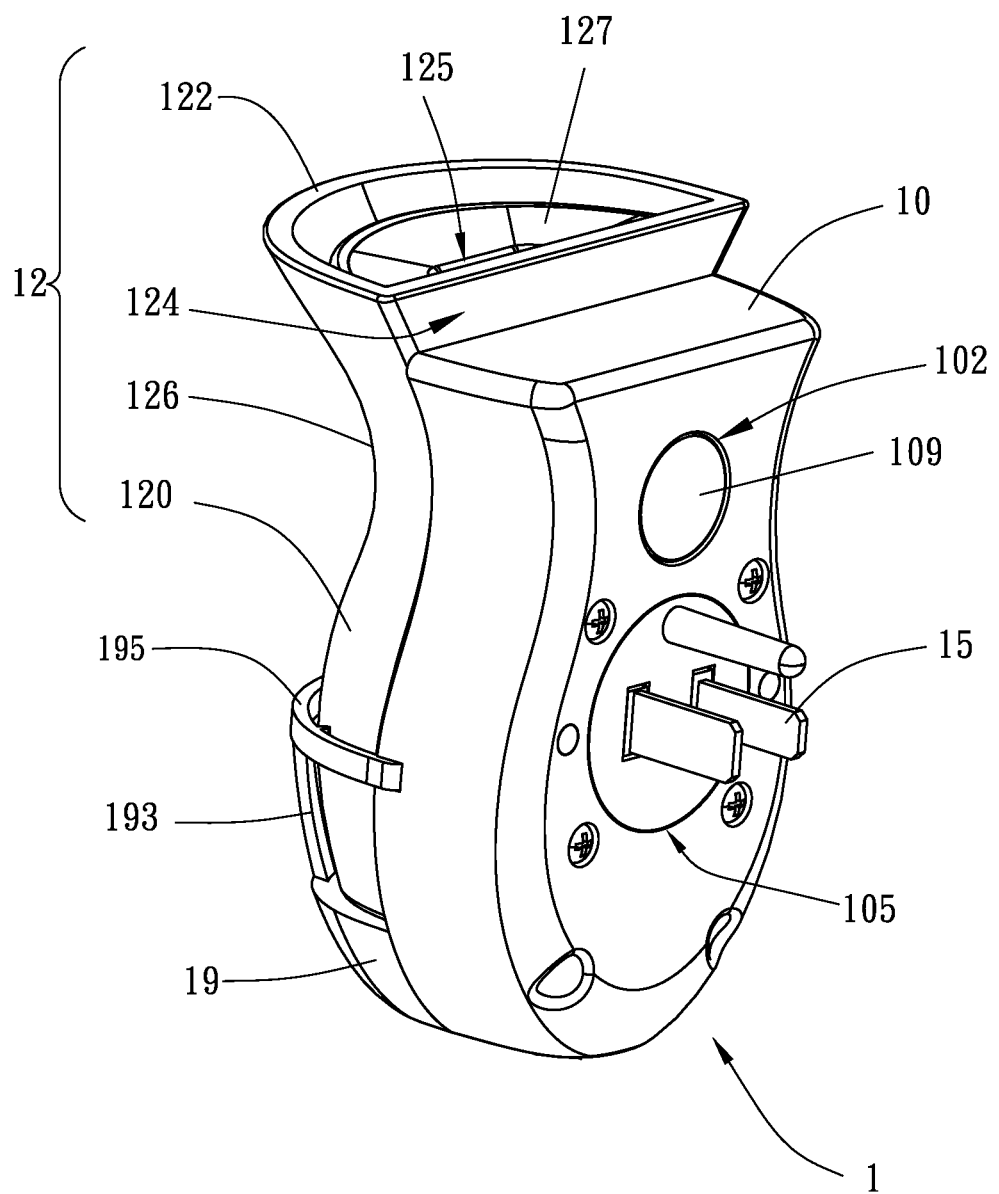
FIG. 6 corresponds to FIG. 4 when viewed from another angle.

Referring to FIG. 6 and FIGS. 2 and 3 again, the carrier 121 loaded aromatic bottle 12 used in the electrical wall socket mounted aroma diffuser 1 is generally required to be inserted into the electrical wall socket aroma diffuser 1 in the upward direction and heated to diffuse the aromatic fluid. However, since the electrical wall socket directions of different countries are different, the electrical plug 15 of the present embodiment is a rotary electrical plug that can change the angle, and the rotary electrical plug is rotatably coupled to the first hole 105 of the back cover 10. The electrical plug 15 can rotatably adjust various angles to suit the plug direction of each country. The rotary electrical plug is rotatably adjusted with respect to the aroma diffuser at various angles to be suitable for plug directions of various countries. Thus, the electrical wall socket mounted aroma diffuser 1 with the carrier loaded aromatic bottle 12 can be kept in the upward direction after installation in an electrical wall socket. In this embodiment, the rotating plug structure of the electrical plug 15 can be rotated, for example, in one direction (for example, by 270 degrees), and can be positioned every time a predetermined angle (such as 90 degrees) is rotated. The electrical plug 15 is provided with a power switch 151 for power on/off control. The power switch 151 is mounted at one side of the electrical plug 15 and electrically connected to the electrical plug 15.

The aromatic fluid can be selected from the group of essential oils, flavors, flower essences, balms, liquid fragrances and sesame oil flavor mixtures. In some embodiments, the aromatic fluid may be injected into the fluid chamber 123 from the filling hole 125 of the carrier 121 using an essential oil or a liquid fragrance diluted with water. The various aromatic fluids are filled in the fluid chamber 123 by the capillary siphon of the pores in the carrier 121. The electrical wall socket mounted aroma diffuser 1 heats the aromatic fluid in the carrier 121 of the carrier loaded aromatic bottle 12 to generate aroma molecules that flow upwardly from the carrier 121 into the surrounding air. The carrier 121 can be used repeatedly with a new supply of aromatic fluid. It is safe and convenient to use. It does not need to clean the part of the aroma diffuser that accommodates the aromatic fluid. The user can detach the carrier 121 loaded aromatic bottle 12 from the bottle holder 19 for the replacement of another carrier loaded aromatic bottle 12 that is filled up with a different smell of aromatic fluid.

Although a particular embodiment of the present invention has been described in detail for purposes of illustration, various modifications and enhancements may be made without departing from the spirit and scope of the invention. Accordingly, the invention is not to be limited except as by the appended claims.

What the invention claimed is:

1. An electrical wall socket mounted aroma diffuser, comprising a back cover, a thermal conduction unit, a heater, an electrical plug, a front cover and a bottle holder, said back cover being a hollow shell, said back cover comprising an opening defined in a front side thereof and a first hole located on an opposing back side thereof to face toward said opening, said front cover being fastened to said front cover to cover said opening, said front cover comprising a second hole, said bottle holder being fastened to an outer side of said front cover, said thermal conduction unit being mounted in said second hole of said front cover in flush with said front cover, said heater being mounted in said back cover and located at an inner side of said thermal conduction unit and kept in contact with said thermal conduction unit, said electrical plug being mounted in said first hole of said back cover and electrically connected with said heater; and a connection means, wherein said back cover further comprises a screw hole disposed adjacent to said first hole at one side; said thermal conduction unit comprises a screw holder located on an inner side thereof, said screw holder having a hole for the passing of said connection means; said heater is disposed between said screw holder and the inner side of said thermal conduction unit said connection means has one end thereof fastened to said screw hole and an opposite end thereof inserted through said screw holder and abutted at said heater against said thermal conduction unit to hold down said heater and said thermal conduction unit.

2. The electrical wall socket mounted aroma diffuser as claimed in claim 1, further comprising a carrier loaded aromatic bottle detachably mounted in said bottle holder with one side thereof in contact with an outer surface of said thermal conduction unit, said carrier loaded aromatic bottle comprising a bottle body, a carrier, a bottle mouth and an aromatic fluid, said carrier being mounted inside said bottle body, said carrier comprising capillary pores for absorbing said aromatic fluid, wherein said electrical plug is used to connect to an external power supply for providing electrical power to said heater.

3. The electrical wall socket mounted aroma diffuser as claimed in claim 2, wherein said carrier of said carrier loaded aromatic bottle comprises a fluid chamber and a filling hole, said fluid chamber being defined in said carrier, said filling hole being located on an upper side of said fluid chamber and disposed in communication with said fluid chamber.

4. The electrical wall socket mounted aroma diffuser as claimed in claim 3, wherein said carrier further comprises a funnel formed on an upper edge thereof, and the filling hole connected to a lower edge of said funnel, said funnel being fitted inside said bottle mouth when said carrier is disposed inside said bottle body.

5. The electrical wall socket mounted aroma diffuser as claimed in claim 4, wherein said bottle body comprises a convergent portion formed on a part thereof; said carrier further comprises a neck located on a bottom side of said funnel, said neck being detachably fitted inside said convergent portion of said bottle body when said carrier is placed in said bottle body from said bottle mouth.

6. The electrical wall socket mounted aroma diffuser as claimed in claim 2, wherein said bottle body further comprises a planar wall formed on one side thereof, said planar wall defining an inner wall on an inner side thereof and an outer wall on an opposing outer side thereof, said outer wall of said planar wall being planarly disposed in contact with an outer surface of said thermal conduction unit; said carrier further comprises a contact plane formed on one side thereof and planarly disposed in contact with said inner wall of said planar wall; said carrier loaded aromatic bottle is detachably mounted in said bottle holder.

7. The electrical wall socket mounted aroma diffuser as claimed in claim 1, wherein said front cover comprises two hook grooves respectively located on two opposite side edges thereof; said bottle holder comprises a base and a fence, said fence comprising an arched rail, said arched rail having two opposite ends thereof respectively terminating in a hook, said hooks of said arched rail being respectively hooked in said hook grooves of said front cover.

8. The electrical wall socket mounted aroma diffuser as claimed in claim 2, wherein said carrier is selected from the group consisting of plastic having pores, polyethylene plastic, porous ceramic, gypsum, suction core, wood and fiber bundle.

9. The electrical wall socket mounted aroma diffuser as claimed in claim 1, wherein said electrical plug is a rotary electrical plug rotatably mounted in said first hole of said back cover.

10. The electrical wall socket mounted aroma diffuser as claimed in claim 1, further comprising a nut and a tamper buckle, said tamper buckle comprising at least one movable fastening member, wherein said back cover further comprises a locating hole disposed in communication with said screw hole and at least one retaining groove formed in said locating hole, locating hole, wherein said connection means is a screw rod, said screw rod of said connection means having one end thereof fastened to said screw hole and said locating hole; said nut is threaded onto said screw rod of said connection means; said tamper buckle is mounted in said locating hole and fastened to an outer side of said nut with said at least one movable fastening member respectively fastened to said at least one retaining groove.

\* \* \* \* \*